United States Patent
Sarac et al.

(10) Patent No.: US 11,312,742 B2
(45) Date of Patent: Apr. 26, 2022

(54) PROCESS FOR PREPARING 3'-O-AMINO-RIBONUCLEOTIDE

(71) Applicant: DNA Script SAS, Le Kremlin-Bicêtre (FR)

(72) Inventors: Ivo Sarac, Le Kremlin-Bicêtre (FR); Cédric Barboux, Le Kremlin-Bicêtre (FR); Supaporn Niyomchon, Le Kremlin-Bicêtre (FR); Florent Beaufils, Le Kremlin-Bicêtre (FR); Martin Bueschleb, Le Kremlin-Bicêtre (FR)

(73) Assignee: DNA Script SAS, Le Kremlin-Bicêtre (FR)

( * ) Notice: Subject to any disclaimer, the term of this patent is extended or adjusted under 35 U.S.C. 154(b) by 0 days.

(21) Appl. No.: 17/431,103

(22) PCT Filed: Feb. 13, 2020

(86) PCT No.: PCT/EP2020/053742
§ 371 (c)(1),
(2) Date: Aug. 13, 2021

(87) PCT Pub. No.: WO2020/165334
PCT Pub. Date: Aug. 20, 2020

(65) Prior Publication Data
US 2022/0041643 A1 Feb. 10, 2022

(30) Foreign Application Priority Data
Feb. 14, 2019 (EP) .................................. EP19305182

(51) Int. Cl.
*C07H 19/06* (2006.01)
*C07H 19/16* (2006.01)
*C07H 1/00* (2006.01)

(52) U.S. Cl.
CPC .............. *C07H 19/06* (2013.01); *C07H 1/00* (2013.01); *C07H 19/16* (2013.01)

(58) Field of Classification Search
None
See application file for complete search history.

(56) References Cited

U.S. PATENT DOCUMENTS 7,544,794 B1 6/2009 Benner
8,212,020 B2 7/2012 Benner et al.

FOREIGN PATENT DOCUMENTS

WO 2013/192078 A1 12/2013

OTHER PUBLICATIONS

Solyev et al., "Optimized synthesis of 3'-O-aminothymidine and evaluation of its oxime derivative as an anti-HIV agent," Heterocyclic Communications, 2015, 21(5):291-295.
International Search Report and Written Opinion of the International Searching Authority for International App No. PCT/EP2020/053742, dated May 26, 2020.

*Primary Examiner* — Layla D Berry
(74) *Attorney, Agent, or Firm* — Gardella Grace P.A.

(57) ABSTRACT

The invention relates to a process for preparing a 3'-O-amino-ribonucleotide. It also relates to a compound of formula (III), and its use as a precursor for the synthesis of a 3'-O-amino-ribonucleotide.

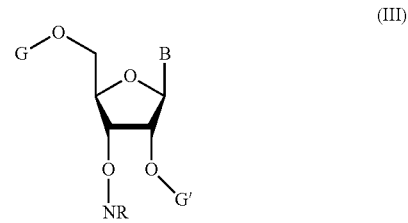

(III)

In formula (III), B is a nitrogenous base or a protected derivative thereof, G and G' are identical or different, and are a protecting group, and RN— is a phthalimido or an imino group.

20 Claims, No Drawings

PROCESS FOR PREPARING 3'-O-AMINO-RIBONUCLEOTIDE

CROSS REFERENCE TO RELATED APPLICATIONS

The present application is a U.S. National Stage Entry of International Application No. PCT/EP2020/053742, entitled "PROCESS FOR PREPARING 3'-O-AMINO-RIBONUCLEOTIDE," filed on Feb. 13, 2020, which claims priority to European Application No. 19305182.8 filed on Feb. 14, 2019. All above-identified applications are hereby incorporated by reference in their entireties.

TECHNICAL FIELD

The invention relates to a process for preparing a 3'-O-amino-ribonucleotide. It also relates to a particular ribonucleoside derivative and its use as a precursor for the synthesis of a 3'-O-amino-ribonucleotide.

TECHNICAL BACKGROUND

Besides their role in the storage, expression and transmission of genetic information, nucleic acids are known for their therapeutic potential. The first strategy, which aimed at treating monogenic diseases by supplementing a defective gene with a "healthy" gene, was extended over the last years, to new therapeutic strategies for treating various diseases, in particular cancers. Breakthroughs in this field are strongly supported by the development of chemical or enzymatic methods for synthetizing nucleic acids. The chemical synthesis of nucleic acids has been the subject of intensive researches since 1950, and has led to more and more efficient strategies. The original use of phosphotriester and H-phosphonate moieties for coupling 3'-hydroxy group of a nucleoside with 5'-hydroxy group of another nucleoside, was later replaced by a phosphoramidite moiety, which is still widely used nowadays. A further improvement was brought by the development of solid support synthesis of nucleic acids, which simplifies the separation of products in the reaction mixture. The enzymatic approach covers a set of techniques, such as polymerase chain reaction (PCR) and rolling circle amplification (RCA), which use a polymerase, a primer, and nucleoside triphosphates. This approach allows to obtain very long chains in a short time, and also to use modified nucleoside triphosphates, provided that said modifications are tolerated by the polymerase. In particular, nucleoside triphosphates are generally subjected to the blocking of their 3'-hydroxy with a removable protecting group or "blocking group". Recently, 3'-O-aminated nucleoside derivatives have sparked scientists' attention due to the great potential of the amino group as blocking group. The amino group is stable and small, which makes it most likely to be accepted by the polymerase. However, one major difficulty lies in the preparation of such a compound, which implies the control of reactions' selectivity relative to hydroxy groups of the ribose unit but also the amino group.

U.S. Pat. Nos. 7,544,794 and 8,212,020 describe the synthesis a 3'-O-amino-2'-deoxyribonucleoside-5'-triphosphate starting from the corresponding 2'-deoxyribonucleoside. The method comprises several steps, and in particular: protecting 5'-hydroxy group, inverting 3'-hydroxy group under Mitsunobu conditions, inserting a —O—NH$_2$ group in the 3' position in a —O-phthalimide "masked" (or "protected") form, deprotecting protected groups, protecting NH$_2$ with an oxime, phosphorylating, and deprotecting the NH$_2$ group.

Regarding ribonucleosides, the presence of a hydroxy group in the 2' position renders the access to the corresponding 3'-O-amino-ribonucleotide more difficult, and therefore, strategies described for deoxyribonucleosides cannot be applied.

Thus, there remains a need to provide a simple and efficient process for preparing 3'-O-amino-ribonucleotide.

SUMMARY OF THE INVENTION

In this respect, the inventors have demonstrated that 3'-O-amino-ribonucleotide can be obtained from 3'-hydroxy-inverted ribonucleoside through a process comprising crucial steps of sulfonylation and reaction with a hydroxyaminated derivative, in particular a N-hydroxy-phthalimide or a N-hydroxy-imine (also called "oxime"). The process developed by the inventors circumvents the difficulty arising from the presence of the 2'-hydroxy group.

Thus, the present invention relates to a process for preparing a 3'-O-amino-ribonucleotide comprising the following successive steps:

(a) reacting a compound of formula (I),

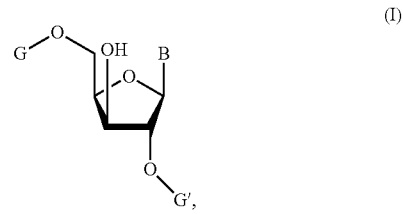

(I)

wherein B represents a nitrogenous base or a protected derivative thereof, and

G and G' are identical or different, and represent a protecting group, with a source of sulfonyl group, under conditions allowing to obtain a compound of formula (II),

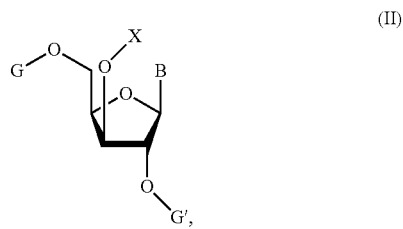

(II)

wherein X represents a sulfonyl group;

(b) reacting the compound of formula (II) obtained in step (a) with a compound RN—OH, wherein RN— represents a phthalimido or an imino group, under conditions allowing to obtain a compound of formula (III),

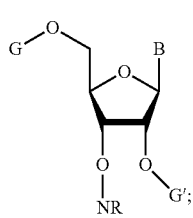

(III)

and (c) converting the compound of formula (III) into the corresponding 3'-O-amino-ribonucleotide.

It also relates to a compound of formula (III),

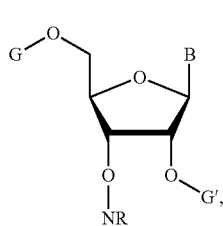

(III)

wherein B represents a nitrogenous base or a protected derivative thereof,

G and G' are identical or different, and represent a protecting group, and

RN— represents a phthalimido or an imino group.

A further object of the present invention is a use of a compound of formula (III) as a precursor for the synthesis of 3'-O-amino-ribonucleotide.

Another object of the present invention is a use of a 3'-O-amino-ribonucleotide obtained by a process as defined above, for the synthesis of a nucleic acid strand.

DETAILED DESCRIPTION OF THE INVENTION

Definitions

According to the present invention, the terms below have the following meanings:

The terms mentioned herein with prefixes such as for example $C_1$-$C_6$, $C_1$-$C_{12}$ or $C_2$-$C_{12}$ can also be used with lower numbers of carbon atoms such as $C_1$-$C_2$, $C_1$-$C_9$, or $C_2$-$C_5$. If, for example, the term $C_1$-$C_6$ is used, it means that the corresponding hydrocarbon chain may comprise from 1 to 6 carbon atoms, especially 1, 2, 3, 4, 5 or 6 carbon atoms. If, for example, the term $C_2$-$C_5$ is used, it means that the corresponding hydrocarbon chain may comprise from 2 to 5 carbon atoms, especially 2, 3, 4, or 5 carbon atoms.

The term "alkyl" refers to a saturated, linear or branched aliphatic group. The term "($C_1$-$C_6$)alkyl" can more specifically refer to methyl, ethyl, propyl, isopropyl, butyl, isobutyl, tert-butyl, pentyl, or hexyl.

The term "cycloalkyl" corresponds to a saturated or unsaturated mono-, bi- or tri-cyclic alkyl group. It also includes fused, bridged, or spiro-connected cycloalkyl groups. The term "($C_3$-$C_{12}$)cycloalkyl" can more specifically refer to cyclopropyl, cyclobutyl, cyclopentyl, and cyclohexyl. The term "cycloalkyl" may also refer to a 5-10 membered bridged carbocyclyl such as bicyclo[2,2,1]heptanyl, or bicyclo[2,2,2]octanyl.

The term "alkoxy" or "alkyloxy" corresponds to the alkyl group as above defined bonded to the molecule by an —O— (ether) bond (in other words, a —O-alkyl group). The term "($C_1$-$C_6$)alkoxy" can more specifically refer to methoxy, ethoxy, propyloxy, isopropyloxy, butyloxy, isobutyloxy, tert-butyloxy, pentyloxy and hexyloxy.

The term "aryl" corresponds to a mono- or bi-cyclic aromatic hydrocarbon group, such as phenyl, biphenyl, or naphthyl.

The term "heterocycloalkyl" corresponds to a saturated or unsaturated cycloalkyl group as above defined further comprising at least one heteroatom or heteroatomic group such as nitrogen, oxygen, or sulphur atom. It also includes fused, bridged, or spiro-connected heterocycloalkyl groups. Representative heterocycloalkyl groups include, but are not limited to 3-dioxolane, benzo [1,3] dioxolyl, pyranyl, tetrahydropyranyl, thiomorpholinyl, pyrazolidinyl, piperidyl, piperazinyl, azepanyl, 1,4-dioxanyl, imidazolinyl, pyrrolinyl, pyrrolidinyl, piperidinyl, imidazolidinyl, morpholinyl, 1,4-dithianyl, pyrrolidinyl, quinolizinyl, oxozolinyl, oxazolidinyl, isoxazolinyl, isoxazolidinyl, thiazolinyl, thiazolidinyl, isothiazolinyl, isothiazolidinyl, dihydropyranyl, tetrahydro-2H-pyranyl, tetrahydrofuranyl, and tetrahydrothiophenyl. The term "heterocycloalkyl" may also refer to a 5-10 membered bridged heterocyclyl such as 7-oxabicyclo[2,2,1]heptanyl.

The term "heteroaryl" as used herein corresponds to an aromatic, mono- or poly-cyclic group comprising between 5 and 14 atoms and comprising one or more heteroatoms, such as nitrogen (N), oxygen (O) or sulphur (S) atom, or heteroatomic groups. Examples of such mono- and poly-cyclic heteroaryl group may be: pyridinyl, thiazolyl, thiophenyl, furanyl, pyrrolyl, imidazolyl, triazolyl, tetrazolyl, benzofuranyl, thianaphthalenyl, indolyl, indolinyl, quinolinyl, isoquinolinyl, benzimidazolyl, triazinyl, thianthrenyl, isobenzofuranyl, phenoxathinyl, isothiazolyl, isoxazolyl, pyrazinyl, pyridazinyl, indolizinyl, isoindolyl, indazolyl, purinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, benzotriazolyl, benzoxazolyl, benzisoxazolyl, oxindolyl, benzothienyl, benzothiazolyl, s-triazinyl, oxazolyl, or thiofuranyl.

The term "halogen" refers to fluorine, chlorine, bromine, or iodine.

Unless otherwise specified, alkyl, cycloalkyl, heterocycloalkyl, alkoxy, aryl and heteroaryl groups as defined above also include the corresponding mono- or poly-substituted groups. Examples of substituents include, but are not limited to, alkyl, cycloalkyl, aryl, F, Cl, Br, I, CN, $NO_2$, $CF_3$, $R^aO$—, $R^bS$—, $R^cNH$— and $R^dR^eN$—, $R^a$, $R^b$, $R^c$, $R^d$ and $R^e$ being each independently selected from H, ($C_1$-$C_6$)alkyl, cycloalkyl, and aryl.

The term "solvent" refers to organic solvent, inorganic solvent such as water, or a mixture thereof. Examples of organic solvents include, but are not limited to, aliphatic hydrocarbons such as pentane or hexane, alicyclic hydrocarbons such as cyclohexane, aromatic hydrocarbons such as benzene, styrene, toluene, ortho-xylene, meta-xylene or para-xylene, halogenated hydrocarbons such as dichloromethane, chloroform or chlorobenzene, nitrogen-based solvents such as pyridine, acetonitrile or triethylamine, oxygen-based solvents, in particular ketones such as acetone, ethers such as diethyl ether, tert-butyl methyl ether (TBME), cyclopentyl methyl ether (CPME), tetrahydrofuran (THF) or methyl tetrahydrofuran (Me-THF), and alcohols such as methanol or ethanol, esters such as n-butyl acetate, or amides such as dimethylformamide (DMF), and mixtures thereof.

The term "acid" refers to a Brønsted or a Lewis acid. Examples of acid include, but are not limited to, hydrochloric acid, hydrobromic acid, hydriodic acid, hydrofluoric acid, nitric acid, sulfuric acid, hexafluorophosphoric acid, tetrafluoroboric acid, trifluoroacetic acid, acetic acid, sulfonic acid such as methanesulfonic acid, mono- or polycarboxylic acid, or mixtures thereof.

The term "base" refers to a Brønsted or a Lewis base. Examples of base include, but are not limited to, hydroxides such as potassium hydroxide or sodium hydroxide, carbonates such as potassium carbonate, sodium carbonate or sodium hydrogenocarbonate, alkoxides such as sodium methoxide, amines such as triethylamine, nitrogen-based cyclic bases, such as imidazole, N-methylimidazole, pyridine or dimethyl-amino-pyridine (DMAP), hydrides such as sodium hydride, and alkylures such as butyllithium.

Conditions (such as temperature, concentration, equivalents of the reactants, solvents) for each step of the process of the invention are described below for particular and/or preferred embodiments, and may be adjusted by the skilled artisan using his/her general background. Each reaction may be treated, and each intermediate or product obtained from a reaction may be isolated, and optionally purified. Alternatively, several steps may be carried out one-pot without treating said reaction and/or isolating said reaction intermediate or reaction product. One or more of the steps may be broken down into substeps. The "treatment" of a reaction refers to the use of reagents such as an acid or a base, and/or solvents, to stop the reaction, and optionally to eliminate all or part of reaction impurities by extraction techniques and washing(s). The "purification" refers to the use of one or more techniques such as recrystallisation or chromatography, aiming at improving the purity (i.e. eliminating further reaction impurities) of the reaction product.

Positions 1' to 5' in the present specification corresponds to positions in the ribose unit, as depicted in the following formula (the stereochemistry is not considered in this formula):

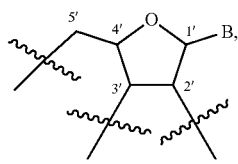

wherein B represents a nitrogenous base.

As stated above, it is the purpose of the present invention to provide a process for preparing a 3'-O-amino-ribonucleotide, said process comprises the following successive steps:

(a) reacting a compound of formula (I),

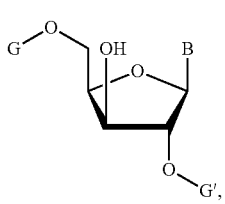

wherein B represents a nitrogenous base or a protected derivative thereof, and

G and G' are identical or different, and represent a protecting group, with a source of sulfonyl group, under conditions allowing to obtain a compound of formula (II),

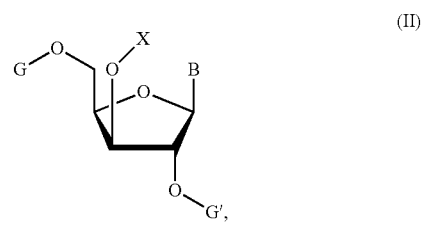

wherein X represents a sulfonyl group;

(b) reacting the compound of formula (II) obtained in step (a) with a compound RN—OH, wherein RN— represents a phthalimido or an imino group, under conditions allowing to obtain a compound of formula (III),

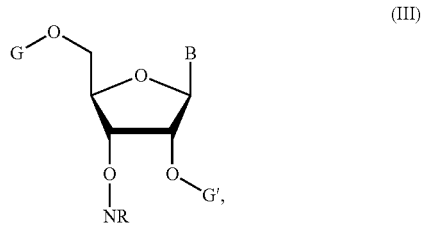

and (c) converting the compound of formula (III) into the corresponding 3'-O-amino-ribonucleotide.

Nitrogenous Base

In the context of the invention, B represents a nitrogenous base or a protected derivative thereof.

The term "nitrogenous base" refers to a purine or pyrimidine base. Examples of purine bases include adenine and guanine. Examples of pyrimidine bases include cytosine, uracil and thymine.

Said nitrogenous base may also be a purine or pyrimidine base in a modified form. Examples of such nitrogenous bases include hypoxanthine, xanthine, 7-methylguanine, 5,6-dihydrouracil, 5-methylcytosine, and 5-hydroxymethylcytosine.

In one embodiment, said nitrogenous base is in a protected form. A "protected derivative" of a nitrogenous base refers to a nitrogenous base in a protected form.

The "protection" refers to the modification of a reactive function of a molecule by introducing a functional group, also called "protecting group", for the purpose of making said reactive function unreactive. The "deprotection" refers to the removal of said functional group, in order to free (i.e. to deprotect) said reactive function.

More particularly, a nitrogenous base having an exocyclic $NH_2$ group, such as cytosine, adenine and guanine, may be in a protected form, through protection of said $NH_2$ group.

Said $NH_2$ group may be protected with an acyl group (i.e. in the form of an amide), or with an amino methylene group (i.e. in the form of an amidine). The protection of said $NH_2$ group with an acyl group may in particular be carried out by reacting the nitrogenous base with a carboxylic acid or a derivative thereof, such as an acyl chloride, an ester or an anhydride, under suitable conditions which can be easily determined by the skilled artisan. Examples of acyl group include, but are not limited to, acyl groups of formula $R^f$—C(O)—, wherein $R^f$ is selected from $(C_1-C_6)$alkyl, $(C_2-C_6)$alkenyl, $(C_2-C_6)$alkynyl, $(C_3-C_{12})$cycloalkyl and aryl. Preferred $R^f$ are methyl, ethyl, iso-propyl, (phenoxy)methyl, (iso-propylphenoxy)methyl, (tert-butylphenoxy)methyl and phenyl.

The protection of said $NH_2$ group with an amino methylene group may in particular be carried out by reacting the nitrogenous base with an acetal, such as a N,N-Dimethylformamide dimethyl acetal, under suitable conditions which can be easily determined by the skilled artisan. Preferred amino methylene group is N,N-dimethylamino methylene group.

Preferably, cytosine is protected with an acyl group of $R^f$—C(O)—, wherein $R^f$ is methyl or phenyl.

Preferably, adenine is protected with an acyl group of $R^f$—C(O)—, wherein $R^f$ is methyl, (phenoxy)methyl or phenyl.

Preferably, guanine is protected with an acyl group of $R^f$—C(O)—, wherein $R^f$ is methyl, iso-propyl, (phenoxy)methyl, (iso-propylphenoxy)methyl or (tert-butylphenoxy)methyl, or with a N,N-dimethylamino methylene group.

A step of deprotecting a protected nitrogenous base may be implemented before, during or after any step of the process according to the invention. Preferably, said step is implemented before step (c) of the process according to the invention, more preferably between step (b) and step (c). Said deprotection may be carried out by using methods well-known to the skilled artisan.

In a particular embodiment, B represents a nitrogenous base selected from the group consisting of adenine, guanine, cytosine, thymine, uracil, and a protected derivative thereof. In preferred embodiment, B represents a nitrogenous base selected from the group consisting of adenine, guanine, cytosine, thymine, and uracil, wherein adenine, guanine, cytosine are in a protected form.

Protecting Groups

In the context of the invention, G and G' are identical or different, and represent a protecting group of hydroxy groups. Examples of such protecting groups include, but are not limited to, trityl (Tr), monomethoxytrityl (MMTr), dimethoxytrityl (DMTr), tert-butyl dimethyl silyl (TBS), tert-butyl diphenyl silyl (TBDPS) or triisopropylsilyl group (TIPS), and (triisopropyl-siloxy)methyl (TOM).

In a preferred embodiment, G and G' are identical or different, and represent a protecting group selected from the group consisting of tert-butyldimethylsilyl (TBS), monomethoxytrityl (MMTr), dimethoxytrityl (DMTr), (triisopropyl-siloxy)methyl (TOM) and triisopropylsilyl (TIPS).

More preferably, G and G' are identical or different, and represent a protecting group selected from the group consisting of tert-butyldimethylsilyl (TBS), monomethoxytrityl (MMTr), and (triisopropyl-siloxy)methyl (TOM).

In a particular embodiment, G and G' are identical, and represent a tert-butyldimethylsilyl (TBS).

In another particular embodiment, G and G' are identical, and represent a monomethoxytrityl (MMTr).

In yet another particular embodiment, G represents a monomethoxytrityl (MMTr) and G' represents a (triisopropyl-siloxy)methyl (TOM), or the reverse.

In yet another particular embodiment, G represents a monomethoxytrityl (MMTr) and G' represents a tert-butyldimethylsilyl (TBS), or the reverse.

Step (a)

According to the invention, a compound of formula (I) is reacted with a source of sulfonyl group(s) under conditions allowing the formation of a compound of formula (II).

A "source of sulfonyl group" refers to a compound comprising one or more sulfonyl group(s) that can be transferred to another compound (more particularly, transferred to the oxygen of a hydroxy group of said other compound, such that a bond is formed between said oxygen and the sulfur atom of the sulfonyl group). Said sulfonyl group is an organic sulfonyl group, which can typically be represented by the formula $R^g$—S(O)$_2$—, $R^g$ being a substituted or unsubstituted, acyclic or cyclic, aliphatic or aromatic hydrocarbon group, optionally comprising heteroatom(s) (such as O, N, S), such as an alkyl, cycloalkyl, heterocycloalkyl, aryl, or heteroaryl.

In particular, said source of sulfonyl group may be a compound of a formula selected among A-Z (or $A^+,Z^-$) and A-O-A, wherein A is a sulfonyl group as defined above and Z is $BF_4$, $PF_6$, $SnCl_5$, $ClO_4$ or a halogen, such as a chlorine.

In a particular embodiment, said sulfonyl group is selected from the group consisting of tosyl (or "toluenesulfonyl", or $R^g$—S(O)$_2$— with $R^g$ being a tolyl), mesyl (or "methanesulfonyl", or $R^g$—S(O)$_2$— with $R^g$ being a methyl), trifluoromethanesulfonyl group ($R^g$—S(O)$_2$— with $R^g$ being a $CF_3$), and any combination thereof. Preferably, said sulfonyl group is tosyl, trifluoromethanesulfonyl, or any combination thereof.

In a particular embodiment, said source of sulfonyl group comprises at least one source of tosyl group, preferably tosyl chloride (or A-Z, with A being tosyl and Z being chloride).

In a particular embodiment, said source of sulfonyl group comprises at least one source of trifluoromethanesulfonyl group, preferably trifluoromethanesulfonyl chloride (or A-Z, with A being trifluoromethanesulfonyl and Z being chloride) and/or trifluoromethanesulfonic anhydride (or A-O-A, with A being trifluoromethanesulfonyl), more preferably trifluoromethanesulfonic anhydride.

In an embodiment, the amount of source of sulfonyl group in step (a) is comprised between 1 and 5 equivalents, preferably between 1 and 3 equivalents, more preferably between 1.5 and 2.5 equivalents, relative to the amount of compound of formula (I).

Step (a) is advantageously carried out in the presence of one or more bases. In a particular embodiment, step (a) is carried out in the presence of triethylamine. The amount of base in step (a) may be comprised between 1 and 20 equivalents, preferably between 5 and 15 equivalents, relative to the amount of compound of formula (I). In a particular embodiment, 10 equivalents triethylamine are used, relative to the amount of compound of formula (I).

The temperature in step (a) is advantageously maintained between −10° C. and 40° C. More particularly, step (a) may be carried out at a temperature comprised between −10° C. and 10° C., upon addition of the source of sulfonyl group to a mixture comprising the compound of formula (I), and then at a temperature comprised between 15° C. and 40° C.

Step (a) leads to a compound of formula (II):

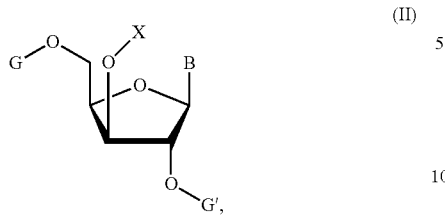

(II)

wherein B, G and G' are as defined above, and X represents a sulfonyl group.

It is understood that, when the source of sulfonyl group is a compound of a formula selected among A-Z (or A⁺,Z⁻⁻) and A-O-A, as defined above, then X in formula (II) is A.

In a preferred embodiment, steps (a) and (b) are carried out successively without purification of the compound of formula (II) obtained in step (a). Preferably, in this embodiment, the compound of formula (II) is subjected to step (b) without purification. In a preferred embodiment, steps (a) and (b) are carried out in "one-pot".

Step (b)

Step (b) comprises reacting the compound of formula (II) obtained in step (a) with a hydroxy-aminated derivative RN—OH, wherein RN— represents an aminated group, particularly a phthalimido or an imino group, under conditions allowing to obtain a compound of formula (III),

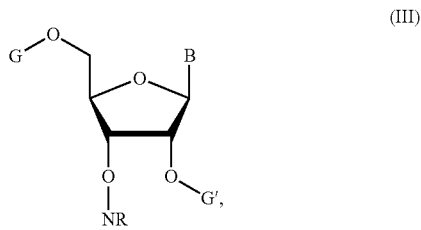

(III)

wherein G, G', B and —NR are as defined above.

In the context of the invention, —NR represents an aminated group.

The term "aminated group" refers to a —NH$_2$ group in a "masked" (or "protected") form. The corresponding —NH$_2$ group can be obtained by deprotecting said aminated group.

In a particular embodiment, —NR represents a phthalimido or an imino group.

The "phthalimido group" can be represented by the following formula:

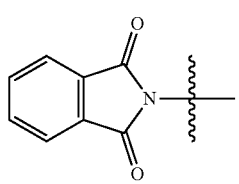

In the present invention, the phthalimido is attached to the rest of the molecule through its N atom.

The term "imino group" refers to a group comprising a C═N bond. In the present invention, the imino group is attached to the rest of the molecule through the N atom of C═N. In a particular embodiment, the imino group is represented by the formula (IV):

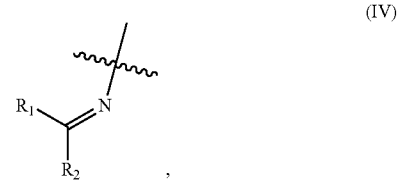

(IV)

wherein R$_1$ and R$_2$ represent independently H, or a substituted or unsubstituted, acyclic or cyclic, aliphatic or aromatic hydrocarbon group, optionally comprising heteroatom(s) (such as O, N, S), such as an alkyl, alkoxy, cycloalkyl, heterocycloalkyl, aryl, or heteroaryl. Preferably, R$_1$ and R$_2$ represent independently H, a (C$_1$-C$_6$)alkyl (e.g. methyl), a (C$_1$-C$_6$)alkoxy (e.g. ethoxy), or an aryl (e.g. phenyl).

In a particular embodiment, RN— is an imino group.

In a preferred embodiment, RN— is a phthalimido group.

The amount of RN—OH in step (b) may be comprised between 1 and 10 equivalents, preferably between 2 and 5 equivalents, relative to the amount of compound of formula (II). In a particular embodiment, 3 equivalents HO-Naphthalimide, relative to the amount of compound of formula (II), are used.

When "the compound obtained of formula (II)" is not isolated and is used as a reference for calculation of equivalents in step (b), said calculation is based on the hypothesis of a total conversion of the compound of formula (I) into the compound of formula (II). This can also be applied for other steps or substeps.

Step (b) is advantageously carried out in the presence of one or more bases. In a particular embodiment, step (b) is carried out in the presence of triethylamine or butyllithium, preferably triethylamine. The amount of base in step (b) may be comprised between 1 and 5 equivalents, preferably between 1 and 2 equivalents, relative to the amount of compound of formula (II). In a particular embodiment, 1.5 equivalents triethylamine, relative to the amount of compound of formula (II), are used.

The temperature in step (b) is advantageously maintained between −10° C. and 40° C. More particularly, step (b) may be carried out at a temperature comprised between −10° C. and 10° C., upon addition of RN—OH to a mixture comprising the compound of formula (II), and then at a temperature comprised between 15° C. and 40° C.

Step (b) leads to the production of a compound of formula (III):

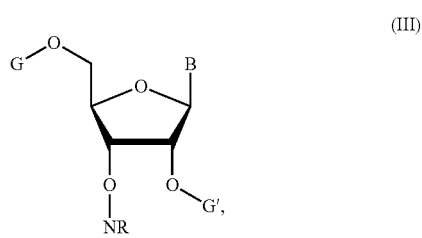

(III)

wherein B, G, G' and —NR are as defined above.

The compound of formula (III) obtained in step (b) is advantageously purified before being subjected to step (c).

Step (c)

Step (c) comprises converting the compound of formula (III) into the corresponding 3'-O-amino-ribonucleotide.

Said 3'-O-amino-ribonucleotide can be represented by the following formula (V):

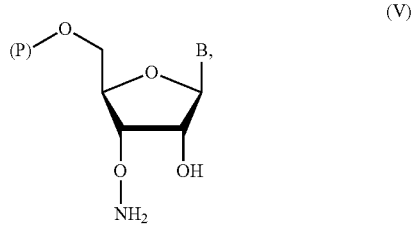

wherein B is as defined above and (P) represents a phosphate group.

Said phosphate may be a monophosphate, diphosphate or triphosphate group, leading respectively to a 5'-mono-, 5'-di- or 5'-tri-phosphorylated 3'-O-amino-ribonucleoside. Preferably, said phosphate is a triphosphate group.

Generally speaking, converting the compound of formula (III) into the corresponding 3'-O-amino-ribonucleotide comprises (the order of the following steps is not considered):
  deprotecting 2'-hydroxy group (i.e. removing protecting group G'),
  deprotecting 5'-hydroxy group (i.e. removing protecting group G),
  converting —NR group into an amino (i.e. —NH$_2$) group, and
  phosphorylating 5'-hydroxy group.

Generally speaking, step (c) comprises the conversion of the 3'-imino group into an amino group.

In a particular embodiment, —NR in the compound of formula (III) obtained in step (b) is a phthalimido group, and step (c) comprises substeps of:
  (c-1) converting the phthalimido group of the compound of formula (III) into an imino group (—NR');
  (c-2) deprotecting 5'-hydroxy group of the compound of formula (III') obtained in step (c-1),

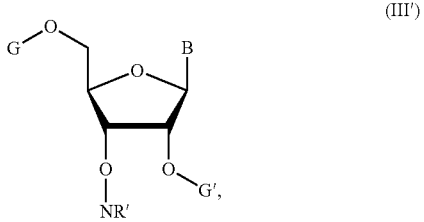

wherein B, G, G' are as defined above, and NR' is an imino group;
  (c-3) phosphorylating 5'-hydroxy group of the compound obtained in step (c-2);
  (c-4) converting the imino group of the compound obtained in step (c-3) into an amino group; wherein 3'-hydroxy group is indifferently deprotected during step (c-2) or after step (c-4).

Alternatively, if the compound of formula (III) already comprises an imino group, thus step (c-2) is directly performed on this compound. In this case, the compound of formula (III') in step (c-2) corresponds to the compound of formula (III) obtained in step (b) (and —NR'=—NR).

Step (c-1) is thus optional, since it depends on the nature of —NR in the compound of formula (III).

In a particular embodiment, the 3'-hydroxy group is deprotected in step (c-2). In such an embodiment, step (c-2) comprises deprotecting both 3'- and 5'-hydroxy groups of the compound of formula (III') (or (III)).

In another particular embodiment, the 3'-hydroxy group is deprotected after step (c-4).

When required, the conversion of the phthalimido group of the compound of formula (III) into an imino group is preferably carried out by:
  (α) reacting the compound of formula (III) with hydrazine, and
  (β) reacting the compound obtained in step (α) with acetone.

Steps (α) and (β) may be carried out successively without purifying the compound obtained in step (α).

Step (α) is advantageously carried out in an organic solvent, preferably ethanol. The temperature in step (α) is advantageously maintained between −10° C. and 50° C., preferably between 10° C. and 30° C.

The amount of hydrazine in step (α) may be comprised between 1 and 5 equivalents, preferably between 1 and 2 equivalents, more preferably between 1 and 1.2 equivalent, relative to the amount of compound of formula (III).

Step (β) is carried out in the presence of acetone, which is advantageously used as solvent and reagent. The temperature in step (β) is advantageously maintained between −10° C. and 50° C., preferably between 10° C. and 30° C.

Converting the phthalimido group of the compound of formula (III) into an imino group leads to the production of a compound of formula (III').

Step (c-2) comprises deprotecting 5'-hydroxy group of said compound of formula (III'), and optionally deprotecting 3'-hydroxy group.

Step (c-2) may be carried out by reacting the compound of formula (III') with a deprotecting reagent. The choice of said deprotecting reagent and the reaction conditions (temperature, solvent, equivalents of deprotecting reagent) depends on G and G', and this choice can be suitably made by the skilled artisan.

In a preferred embodiment, G and G' are tert-butyldimethylsilyl groups and said deprotecting reagent in step (c-2) is a fluoride source.

The term "fluoride source" refers to one or more reagents which are able to formally transfer a fluoride anion (F$^-$) to another compound. Examples of fluoride sources include, but are not limited to, hydrogen fluoride, hydrogen fluoride pyridine, silver fluoride, cesium fluoride, potassium fluoride, tetramethylammonium fluoride, tetrabutylammonium fluoride (TBAF), and ammonium fluoride (NH$_4$F).

Preferably, said fluoride source is tetrabutylammonium fluoride, ammonium fluoride or any combination thereof, and more preferably ammonium fluoride.

Alternatively, G and G' may be monomethoxytrityl groups, and said deprotecting reagent in step (c-2) may be a combination of trifluoroacetic acid and triisopropylsilane.

Step (c-2) is advantageously carried out in an organic solvent, such as methanol or dichloromethane. The temperature in step (c-2) is advantageously maintained between −10° C. and 50° C., preferably between 10° C. and 30° C.

Step (c-3) comprises phosphorylating 5'-hydroxy group of the compound obtained in step (c-2), and preferably triphosphorylating said group.

Step (c-3) may particularly comprise the following substeps of
(γ) reacting the compound obtained in step (c-2) with 2-chloro-1,3,2-benzodioxaphosphorin-4-one or phosphoryl chloride; and
(δ) reacting the compound obtained in step (γ) with a pyrophosphate salt.

Said 2-chloro-1,3,2-benzodioxaphosphorin-4-one or phosphoryl chloride may be used pure or diluted. Preferably, said 2-chloro-1,3,2-benzodioxaphosphorin-4-one or phosphoryl chloride is used diluted in one or more organic solvents such as dioxane and/or pyridine.

The amount of 2-chloro-1,3,2-benzodioxaphosphorin-4-one or phosphoryl chloride in step (γ) may be comprised between 1 and 2 equivalents, preferably between 1.2 and 1.6 equivalents, relative to the amount of compound obtained in step (c-2).

Pyrophosphate salts include, but are not limited to, an alkali metal pyrophosphate such as sodium pyrophosphate, an alkali earth metal pyrophosphate such as calcium pyrophosphate, an ammonium pyrophosphate, in particular tri($C_1$-$C_{12}$)alkylammonium pyrophosphate such as tributylammonium pyrophosphate, and a mixture thereof.

In one preferred embodiment, said pyrophosphate salt is an ammonium pyrophosphate, preferably tributylammonium pyrophosphate. Said ammonium pyrophosphate may result from mixing an alkali metal pyrophosphate or an alkali earth metal pyrophosphate, with an ammonium salt, in particular ammonium bicarbonate, ammonium chloride, ammonium bromide, ammonium iodide, ammonium hexafluorophosphate, ammonium tetrafluoroborate, in particular a tri($C_1$-$C_{12}$)alkylammonium salt such as tributylammonium bicarbonate.

Said pyrophosphate salt may be used pure or diluted. Preferably, said pyrophosphate salt is used diluted in one or more organic solvents such as DMF. The amount of pyrophosphate salt in step (δ) may be comprised between 1 and 5 equivalents, preferably between 1.5 and 3 equivalents, relative to the amount of compound obtained in step (γ).

Step (δ) may be carried out in the presence of an amine, such as tributylamine.

In a particular embodiment, step (δ) described above is followed by step (ε) which consists in reacting the compound obtained in step (δ) with a mixture comprising iodine, pyridine and water.

Steps (γ), (δ) and (ε) may be each independently carried out at a temperature maintained between 5 and 45° C., preferably between 15 and 30° C.

Step (c-4) comprises converting the imino group of the compound obtained in step (c-3) into an amino group.

Said step (c-4) may be carried out by reacting the compound obtained in step (c-3) with an acid, such as acetic acid or a buffered solution thereof. The pH value is in the range of 1-6, preferably between 4-6. Said acid may be in the form of a pure gas, liquid or solid, or may be solubilized in a solvent such as water or dioxane. Step (c-3) is advantageously carried out in an aqueous solvent, such as water. The temperature in step (c-3) is advantageously maintained between −10° C. and 50° C., preferably between 10° C. and 30° C.

Preparation of the Compound of Formula (I):

In a particular embodiment, the compound of formula (I) as defined above, is obtained by the following successive steps:

(A) protecting 2'- and 5'-hydroxy groups of a ribonucleoside of formula (I.1)

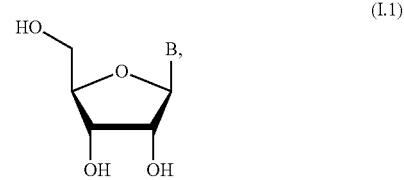

(I.1)

under conditions allowing to obtain a compound of formula (I.2),

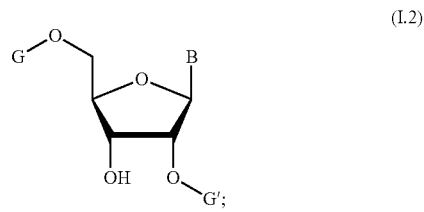

(I.2)

and (B) inverting 3'-hydroxy group of the compound of formula (I.2), under conditions allowing to obtain a compound of formula (I), wherein G, G' and B in formulae (I.1) and (I.2) are as defined above for formula (I).

As stated above, B may be a nitrogenous base in a protected form.

A process for protecting the nitrogenous base B of a ribonucleoside of formula (I.1) can comprise the steps of:

(p1) protecting 2'-, 3'-, and 5'-hydroxy groups of a ribonucleoside of formula (I.1), wherein B is in a non-protected form, with a silyl group such as trimethylsilyl, preferably by reacting said 2'-deoxyribonucleoside with a suitable silylation reagent such as trimethylsilyl chloride;

(p2) protecting the $NH_2$ group of the non-protected nitrogenous base B of the compound obtained in step (p2) with an acyl group or with amino methylene group;

(p3) deprotecting 2'-, 3'-, and 5'-hydroxy groups of the compound obtained in step (p2), preferably by reacting said compound with ammonium hydroxide;

thereby allowing to obtain a ribonucleoside of formula (I.1), wherein B is in a protected form.

Step (A) comprises protecting 2'- and 5'-hydroxy groups of a ribonucleoside of formula (I.1),

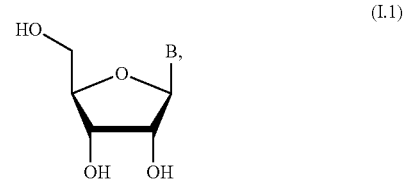

(I.1)

under conditions allowing to obtain a compound of formula (I.2),

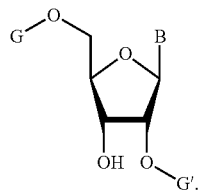

Step (A) may be carried out by reacting the compound of formula (I.1) with one or more protecting reagents, which are sources of the protecting groups G and G'. Said sources of protecting groups G and G' may advantageously be respectively of formulae G-Y and G'-Y', wherein:

G and G' are as defined above,

Y and Y' are identical or different, and represent $BF_4$, $PF_6$, $CF_3SO_3$, $SnCl_5$, $ClO_4$ or a halogen, such as a chlorine or bromine. In a preferred embodiment, Y and Y' are chlorine.

In a preferred embodiment, G-Y and G'-Y' are independently selected from tert-butyldimethylsilyl chloride (TBS-Cl), monomethoxytrityl chloride (MMTr-Cl), dimethoxytrityl (DMTr-Cl), (triisopropyl-siloxy)methyl (TOM-Cl) and triisopropylsilyl (TIPS-Cl).

More preferably, G-Y and G'-Y' are independently selected from tert-butyldimethylsilyl chloride (TBS-Cl), monomethoxytrityl chloride (MMTr-Cl), and (triisopropyl-siloxy)methyl chloride (TOM-Cl).

In an embodiment, where G and G' are different (Y and Y' being identical or different), step (A) is preferably broken down into two substeps consisting in:

(A-1) protecting the 5'-hydroxy group of compound of formula (I-1), typically by reacting said compound with a source of protecting group G, such as G-Y; and (A-2) protecting the 2'-hydroxy group of compound obtained in step (A-1), typically by reacting said compound with a source of protecting group G', such as G'-Y'.

In a particular embodiment, G-Y and G'-Y' are both tert-butyldimethylsilyl chloride (TBS-Cl).

In another particular embodiment, G-Y and G'-Y' are both monomethoxytrityl chloride (MMTr-Cl).

In yet another particular embodiment, G-Y is monomethoxytrityl chloride (MMTr-Cl) and G'-Y' is (triisopropyl-siloxy)methyl chloride (TOM-Cl), or the reverse.

In yet another particular embodiment, G-Y is monomethoxytrityl chloride (MMTr-Cl) and G'-Y' is a tert-butyldimethylsilyl chloride (TBS-Cl), or the reverse.

In an embodiment, where G-Y and/or G'-Y' are TBS-Cl, step (A) (or substeps (A-1) and/or (A-2)), may be carried out in the presence of
a base such as pyridine, and/or
a silver salt such as silver nitrate.

In an embodiment, where G-Y and/or G'-Y' are TOM-Cl, step (A) (or substeps (A-1) and/or (A-2)), may be carried out in the presence of:
a base, such as diisopropylethylamine (DIPEA), and/or
an organotin compound, such as $Bu_2SnCl_2$.

An "organotin compound" refers to a compound having at least one C—Sn bond.

In an embodiment, where G-Y and/or G'-Y' are MMTr-Cl, step (A) (or substeps (A-1) and/or (A-2)), may be carried out in the presence of a base, such as pyridine.

Step (A) is advantageously carried out in an organic solvent, such as THF. The temperature in step (A) is advantageously maintained between −10° C. and 50° C., preferably between 10° C. and 30° C.

Step (A) leads to the production of a compound a formula (I-2),

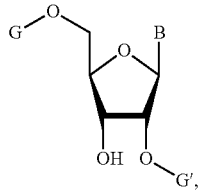

wherein G, G' and B are as defined above.

Step (B) comprises inverting 3'-hydroxy group of the compound of formula (I.2), under conditions allowing to obtain a compound of formula (I).

The expressions "inverting a group" or "inversion of a group" refer to inverting the stereochemical configuration (i.e. from (R) to (S) or from (S) to (R)) of the stereogenic carbon substituted by said group.

Preferably, step (B) comprises the following substeps:

(B-1) oxidizing 3'-hydroxy group of the compound of formula (I.2) into a ketone group, by use of an oxidizing agent, (B-2) reducing the ketone group of the compound obtained in step (B-1), by means of a hydride source, preferably sodium borohydride, so as to obtain the compound of formula (I).

An "oxidizing agent" refers herein to one or more organic or inorganic compounds which are able, individually or in combination, to convert an alcohol group into a ketone group. Examples of such oxidizing agent include, but are not limited to, Dess-Martin periodinane (DMP), 2-iodoxybenzoic acid (IBX), pyridinium dichromate (PDC), pyridinium chlorochromate (PCC), Jones' reagent, Collins' reagent, Swern reagents, Moffat reagents, Oppenauer reagents (Al $(OiBu)_3$+acetone), and any combination thereof.

In a preferred embodiment, said oxidizing agent is DMP or PDC.

Step (B-1) is advantageously carried out in an organic solvent, such as dichloromethane and/or tert-butanol. The temperature in step (B-1) is advantageously maintained between −10° C. and 50° C., preferably between 10° C. and 30° C. The amount of said oxidizing agent in step (B-1) may be comprised between 1 and 10 equivalents, preferably between 1 and 5 equivalents, more preferably between 1 and 2 equivalents, relative to the amount of compound of formula (I-2).

A "hydride source" refers to one or more reagents which are able to (formally) transfer one or more hydrides (H⁻) to another compound, resulting in a reduction of said other compound (more particularly, a reduction of a ketone group of said other compound into an alcohol group).

Examples of hydride sources include, but are not limited to, lithium aluminum hydride, $LiAlH(OMe)_3$, sodium or potassium borohydride, zinc borohydride, dihydrogen, borane ($BH_3$), diborane ($B_2H_6$), 9-borabicyclo[3.3.1]nonane (9-BBN), monoisopinocampheylborane, dicyclohexylborane, dimesitylborane, disiamylborane, catecholborane, pinacolborane, L-selectride, and any combination thereof.

In a preferred embodiment, said hydride source is sodium borohydride.

Step (B-2) is advantageously carried out in an organic solvent, such as methanol or THF. The temperature in step (B-2) is advantageously maintained between −10° C. and 50° C., preferably between 10° C. and 30° C. The amount of said hydride source in step (B-2) may be comprised between 1 and 10 equivalents, preferably between 1 and 5 equivalents, more preferably between 1 and 2 equivalents, relative to the amount of compound obtained in step (B-1).

Implementation of step (B) leads to the production of a compound of formula (I) as defined above.

Compound of Formula (II):

The invention also relates to a compound of formula (III),

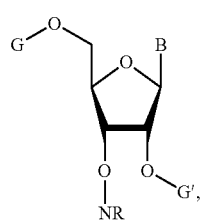

(III)

wherein B represents a nitrogenous base or a protected derivative thereof,
G and G' are identical or different, and represent a protecting group, and
RN— represents a phthalimido or an imino group.

In a preferred embodiment, the compound according to the invention is a compound of formula (III) wherein at least one of the following features is fulfilled:
B represents a nitrogenous base selected from the group consisting of adenine, guanine, cytosine, thymine, uracil, and a protected derivative thereof; and/or
G and G' are identical or different, and represent a protecting group selected from the group consisting of tert-butyldimethylsilyl, monomethoxytrityl, and (triisopropyl-siloxy)methyl; and/or
RN— represents an imino group of formula (IV),

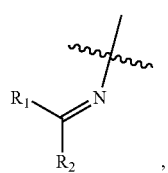

(IV)

wherein $R_1$ and $R_2$ represent independently H, a ($C_1$-$C_6$) alkyl, a ($C_1$-$C_6$)alkoxy, or an aryl.

In another embodiment, RN— is a phthalimido group.

A process for preparing a compound of formula (III) advantageously comprises steps (a) and (b) as described above.

Another object of the present invention is a use of a compound of formula (III) as a precursor for the synthesis of 3'-O-amino-ribonucleotide.

A further object of the present invention is a use of a 3'-O-amino-ribonucleotide obtained by a process of the invention, for the synthesis of a nucleic acid strand.

In the context of the invention, a "nucleic acid strand" refers to an oligonucleotide sequence having at least two nucleotides. In a particular embodiment, said nucleic acid strand is a RNA (RiboNucleic Acid) strand, a DNA (DeoxyriboNucleic Acid) strand, or a hydride strand thereof.

A hydride of a DNA and a RNA strand refers to a oligonucleotide sequence having at least one ribonucleotide and at least one deoxyribonucleotide.

In a preferred embodiment, said nucleic acid strand is a RNA strand.

A method for preparing a nucleic acid strand comprising at least one 3'-O-amino-ribonucleotide obtained by a process of the invention, may comprise the steps of
(1) coupling a 3'-O-amino-ribonucleotide with a 3'-hydroxy group of a nucleotide of a nucleic acid, by means an enzyme; and
(2) cleaving O—N bond of 3'-O-amino-ribonucleotide coupled in step (1), so as to deprotect the corresponding 3'-hydroxy group;

wherein steps 1 and 2 are cyclically carried out n times, n being an integer higher than or equal to 1.

In a particular embodiment, said "nucleotide of a nucleic acid is a ribonucleotide or a deoxyribonucleotide of a nucleic acid. In a preferred embodiment, said "nucleotide of a nucleic acid" is a ribonucleotide of a nucleic acid.

In said method composed of n cycles, wherein n is as defined above, it is understood that the 3'-O-amino-ribonucleotide engaged in step (1) of a cycle ("cycle k", wherein k is an integer comprised between 1 and n) may be identical to or different from the 3'-O-amino-ribonucleotide engaged in step (1) of the preceding cycle ("cycle k−1").

In said method composed of n cycles, wherein n is as defined above, it is also understood that the 3'-hydroxy group deprotected in step (2) of a cycle ("cycle k", wherein k is an integer comprised between 1 and n−1) corresponds to the 3'-hydroxy group coupled with a 3'-O-amino-ribonucleotide, in step (1) of the next cycle ("cycle k+1").

Said enzyme in step (1) is advantageously a polymerase.

Step (2) of cleaving O—N bond may be carried out by use of a cleaving reagent. More specifically, said 3'-O-amino-ribonucleotide coupled in step (1) may be contacted with a cleaving reagent such as an oxidizing reagent or a reducing agent. The O—$NH_2$ group may be converted into a more reactive group such as a diazo compound, an O-alkylhydroxamic acid or an oxime, before or during being contacted with said cleaving reagent.

Examples of oxidizing agents include, but are not limited to, hypochlorite, nitric oxide, nitrous acid, nitrite ester, nitrosating agents, N-bromosuccinimide and N-bromoacetamide.

Examples of reducing agents include, but are not limited to, sodium amalgam, titanium (III) chloride, molybdenum hexacarbonyl, divalent vanadium, samarium, and a combination of hydrogen with a catalyst, such as a Pt or Pd catalyst.

Other type of cleaving reagents may be used, such as cupferron, acid blue 45, N-nitrosopyrrolidine, quinone, nitrobenzene or nitroolefins.

The invention claimed is:
1. A process for preparing a 3'-O-amino-ribonucleotide, comprising the steps of:
   (a) reacting a compound of formula (I)

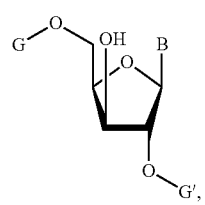

(I)

with a source of sulfonyl group(s), under conditions allowing to obtain a compound of formula (II),

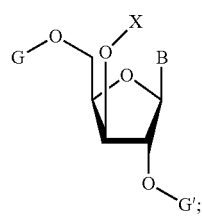

(II)

(b) reacting the compound of formula (II) obtained in step (a) with a compound RN—OH, wherein RN— is a phthalimido or an imino group, under conditions to obtain a compound of formula (III),

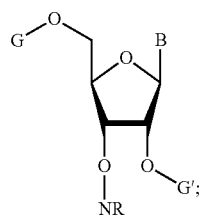

(III)

and
   (c) converting the compound of formula (III) into the corresponding 3'-O-amino-ribonucleotide;
wherein
   B is a nitrogenous base or a protected derivative thereof,
   G and G' are identical or different, and are each a protecting group, and
   X is a sulfonyl group.

2. The process according to claim 1, wherein B is a nitrogenous base selected from the group consisting of adenine, guanine, cytosine, thymine, uracil, and a protected derivative thereof.

3. The process according to claim 1, wherein the sulfonyl group(s) are selected from the group consisting of tosyl, mesyl, trifluoromethanesulfonyl group, and any combination thereof.

4. The process according to claim 1, wherein the source of sulfonyl group(s) comprises tosyl chloride.

5. The process according to claim 1, wherein the source of sulfonyl group(s) comprises trifluoromethanesulfonyl chloride and/or trifluoromethanesulfonic anhydride.

6. The process according to claim 1, wherein G and G' are identical or different, and are a protecting group selected from the group consisting of tert-butyldimethylsilyl (TBS), monomethoxytrityl (MMTr), dimethoxytrityl (DMTr), (tri-isopropyl-siloxy)methyl (TOM), and triisopropylsilyl (TIPS).

7. The process according to claim 1, wherein RN— is an imino group of formula (IV),

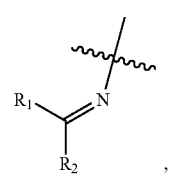

(IV)

wherein $R_1$ and $R_2$ are independently selected from the group consisting of H, a $(C_1-C_6)$alkyl, a $(C_1-C_6)$alkoxy, and an aryl.

8. The process according to claim 1, wherein the compound of formula (I) is prepared by the process, comprising the steps of:
   (A) reacting a ribonucleoside of formula (I.1),

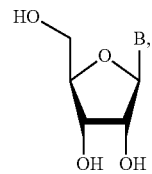

(I.1)

with one or more sources of protecting groups G and G', under conditions to obtain a compound of formula (I.2), wherein the 2'- and 5'-hydroxy groups are protected:

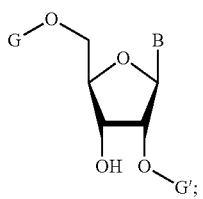

(I.2)

(B) inverting the 3'-hydroxy group of the compound of formula (I.2), under conditions to obtain a compound of formula (I).

9. The process according to claim 8, wherein step (B) comprises the substeps:
   (B-1) oxidizing the 3'-hydroxy group of the compound of formula (I.2) into a ketone group, by means of an oxidizing agent; and
   (B-2) reducing the ketone group of the compound obtained in step (B-1), by means of a hydride source, to obtain the compound of formula (I).

10. The process according to claim 1, wherein step (c) comprises the substeps:
   (c-1) converting the phthalimido group of the compound of formula (III) into an imino group;

(c-2) deprotecting the 5'-hydroxy group of a compound of formula (III'),

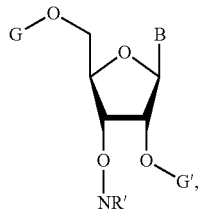

(III')

wherein NR' is an imino group;
(c-3) phosphorylating the 5'-hydroxy group of the compound obtained in step (c-2); and
(c-4) converting the imino group of the compound obtained in step (c-3) into an amino group;
wherein the 3'-hydroxy group is deprotected in step (c-2) or after step (c-4).

11. A compound of formula (III),

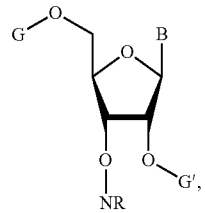

(III)

wherein B is a nitrogenous base or a protected derivative thereof,
G and G' are identical or different, and are a protecting group, and
RN— is a phthalimido or an imino group.

12. The compound according to claim 11, wherein at least one of the following features is met:
B is a nitrogenous base selected from the group consisting of adenine, guanine, cytosine, thymine, uracil, and a protected derivative thereof;
G and G' are identical or different, and are a protecting group selected from the group consisting of tert-butyldimethylsilyl, monomethoxytrityl, and (triisopropyl-siloxy)methyl; and
RN— is an imino group of formula (IV),

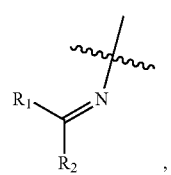

(IV)

wherein $R_1$ and $R_2$ are independently selected from the group consisting of: H, a $(C_1\text{-}C_6)$alkyl, a $(C_1\text{-}C_6)$ alkoxy, and an aryl.

13. The process according to claim 1, wherein the source of sulfonyl group(s) comprises trifluoromethanesulfonic anhydride.

14. The process according to claim 9, wherein:
the oxidizing agent is selected from the group consisting of: Dess-Martin periodinane and pyridinium dichromate, and
the hydride source is sodium borohydride.

15. The compound according to claim 11, wherein B is a nitrogenous base selected from the group consisting of adenine, guanine, cytosine, thymine, uracil, and a protected derivative thereof.

16. The compound according to claim 11, wherein G and G' are identical or different, and are a protecting group selected from the group consisting of tert-butyldimethylsilyl, monomethoxytrityl, and (triisopropyl-siloxy)methyl.

17. The compound according to claim 11, wherein RN— is an imino group of formula (IV),

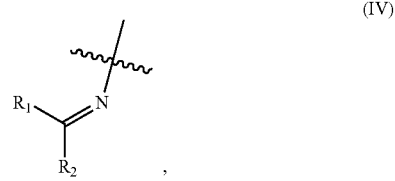

(IV)

wherein $R_1$ and $R_2$ are independently selected from the group consisting of: H, a $(C_1\text{-}C_6)$alkyl, a $(C_1\text{-}C_6)$ alkoxy, and an aryl.

18. The compound according to claim 11, wherein:
B is a nitrogenous base selected from the group consisting of adenine, guanine, cytosine, thymine, uracil, and a protected derivative thereof;
G and G' are identical or different, and are a protecting group selected from the group consisting of tert-butyldimethylsilyl, monomethoxytrityl, and (triisopropyl-siloxy)methyl; and
RN— is an imino group of formula (IV),

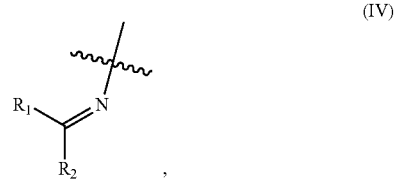

(IV)

wherein $R_1$ and $R_2$ are independently selected from the group consisting of: H, a $(C_1\text{-}C_6)$alkyl, a $(C_1\text{-}C_6)$ alkoxy, and an aryl.

19. The compound according to claim 18, wherein:
B is a nitrogenous base selected from the group consisting of adenine, guanine, cytosine, thymine, and uracil; and
the exocyclic $NH_2$ groups of adenine, guanine, and cytosine are protected by an acyl group, $R^f$—C(O)—, wherein $R^f$ is selected from the group consisting of $(C_1\text{-}C_6)$alkyl, $(C_2\text{-}C_6)$alkenyl, $(C_2\text{-}C_6)$alkynyl, $(C_3\text{-}C_{12})$cycloalkyl and aryl.

20. The compound according to claim 18, wherein:
B is a nitrogenous base selected from the group consisting of adenine, guanine, cytosine, thymine, and uracil; and
the exocyclic $NH_2$ groups of adenine, guanine, and cytosine are protected by an acyl group, $R^f$—C(O)—, wherein $R^f$ is selected from the group consisting of $(C_1\text{-}C_6)$alkyl, $(C_2\text{-}C_6)$alkenyl, $(C_2\text{-}C_6)$alkynyl, $(C_3\text{-}C_{12})$cycloalkyl and aryl.

* * * * *